(12) United States Patent
Abdel-Rahman

(10) Patent No.: US 6,207,049 B1
(45) Date of Patent: Mar. 27, 2001

(54) MULTICHANNEL CAPILLARY COLUMN

(75) Inventor: Mahmoud F. Abdel-Rahman, West Grove, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/364,723

(22) Filed: Jul. 30, 1999

(51) Int. Cl.[7] .................................................. B01D 15/08
(52) U.S. Cl. ........................ 210/198.2; 96/101; 65/86; 138/111; 422/70
(58) Field of Search ................... 210/198.2, 502.1, 210/656, 657; 96/101; 422/70; 65/86; 138/111, 115

(56) References Cited

U.S. PATENT DOCUMENTS

| | | | |
|---|---|---|---|
| 4,208,284 | * 6/1980 | Pretorius et al. | 210/198.2 |
| 4,293,415 | 10/1981 | Bente et al. | 210/198.2 |
| 4,424,127 | 1/1984 | Roeraade | 210/98.2 |
| 4,818,264 | 4/1989 | Langhorst | 65/4.3 |
| 5,864,743 | 1/1999 | Tuchinskiy et al. | 419/2 |

OTHER PUBLICATIONS

Bulletin #356, "Alltech Multi–Cap(TM) Capillary Columns", Alltech Associates, Inc., 1997, pp. 1–7.

* cited by examiner

Primary Examiner—Joseph W. Drodge

(57) ABSTRACT

A multichannel capillary column having an interior wall defining a single internal bore, wherein the interior wall defines a plurality of n channels and n ridges, wherein adjacent channels are partially separated by a respectively interposed ridge, and wherein a central, coaxial portion of the internal bore allows cross-channel fluid communication between all of the n channels.

9 Claims, 1 Drawing Sheet

MULTICHANNEL CAPILLARY COLUMN

FIELD OF THE INVENTION

The present invention relates to an analytical instrument, and more particularly to a column for performing capillary chromatographic separations useful in, for example, high performance gas and liquid chromatography, or capillary electro-chromatography, or supercritical chromatography.

BACKGROUND OF THE INVENTION

Analytical instruments which detect one or more characteristics of a fluid are commonly employed in a wide variety of applications, such as sample purification, chemical analysis, clinical assay, and industrial processing. Gas and liquid chromatographs are particular examples of analytical instruments wherein certain characteristics related to a particular fluid are detected, e.g., the presence or absence of a fluid component, such as an analyte or contaminant.

Capillary chromatographic separation methods are preferably performed in synthetic fused silica tubing with internal diameters ranging from 5 to 530 micrometers. Such tubing consists of a silica ($SiO_2$) glass drawn at high temperature from a quartz preform provided with a protective outside layer such as polyamide or aluminum. See, for example, U.S. Pat. No. 4,293,415, issued to Dandeneau et al., which disclosed the use of a fused silica capillary having wall coatings on the inside surface to stimulate specific interactions when employed in open tubular capillary gas or liquid chromatography, for open tubular supercritical fluid chromatography. Fused silica capillary columns are also known for use in capillary electrophoresis and capillary electro-chromatography.

The resolution of a capillary column, and the time required for carrying out a separation, are functions of several interrelated column and operational parameters. The major factors that influence a separation are: column internal diameter, column length, the type of stationary phase and its film thickness, the type of carrier gas, the carrier gas velocity, and the column temperature. Among these factors, a reduction in the column length is understood to decrease the analysis time, but at the expense of resolution. For fast capillary gas chromatography without a significant loss in resolution, the column internal diameter is typically reduced to 0.1 mm or less. Hence, there are advantages and limitations in the use of narrow-bore well coated open tubular column (WCOT) for high-speed capillary gas chromatography. In a typical example for use in current instrumentation, a 100 micrometer internal diameter column of 5 to 10 meters in length may be used.

However, the most serious limitation of the reduced diameter column is its associated decrease in sample capacity. Capacity is known as the ability of a column to tolerate high concentrations of solutes. Degradation of chromatographic performance is observed when the column capacity is exceeded. This condition is commonly referred to as "overload" and is indicated by peak broadening and asymmetry. Sample capacity is also related to the film thickness and phase ratio. Thus, a chromatographer will expect a limit in the sample capacity that is set according to the internal diameter for a given phase ratio or film thickness. Small diameter (<0.2 mm internal diameter) columns will offer the advantages of high-efficiency and high-resolution, but at the expense of sample capacity. Low resolution, wide-bore fused silica columns have a much higher sample capacity and are typically employed for performing simple, packed-column separations. Accordingly, the elements of efficiency, speed, capacity, and resolution are factors which must be balanced when optimizing a chromatographic separation.

Accordingly, it would be desirable to employ a capillary column suited for use in the aforementioned modes of chromatography that has the practical advantages of a relatively large internal diameter column (and in particular, its capacity) but also exhibits the high resolution and the rapid analysis obtained by a relatively small internal diameter column.

One approach has been to assemble a plurality of parallel, narrow-bore capillary columns, in which each of the columns presumably have identical properties, in an attempt to eliminate the disadvantage residing in the limited capacity of the narrow-bore capillary column. By using a larger number of such capillary columns coupled in parallel, one would expect to separate large quantities of samples while maintaining the aggregate abilities of each of the capillary columns. However, this proposed "multi-capillary" column device has not been found to be practically useful, due largely in part to the difficulty in providing a column composed of several capillaries coupled in parallel, wherein the individual capillaries exhibit identical behavior. Some examples of the causes of differences that may arise in the performance of individual capillaries are: deformation of the capillaries in different amounts depending on their position in the composite column assembly; temperature gradients over the cross-section of the column (wherein it is difficult to change the temperature of the column without causing radial temperature gradients which subsequently result in different separation rates of the different capillaries); differing stationary phase thicknesses; disparity in column aging, etc. See, for example, U.S. Pat. Nos. 4,424,127 and 4,818, 264.

SUMMARY OF THE INVENTION

The advantages of the invention are achieved in a multichannel capillary column suitable for use in an analytical instrument.

A preferred embodiment of the multichannel capillary column includes an interior wall defining a single internal bore, wherein the interior wall comprises a plurality of n channels and n ridges and the adjacent channels are partially separated by a respectively interposed ridge, and wherein a central, coaxial portion of the internal bore communicates with each of the channels to allow cross-channel fluid communication between all of the n channels.

In a first aspect of the present invention, the multichannel capillary column includes a single internal bore optionally having an internal coating of stationary phase on the interior wall, thus enabling its use as a well-coated open tubular separation column for performing an analysis of a large volume of sample at high speed without diminished resolution.

In another aspect of the present invention, the interior wall offers an increase in the total surface area of the stationary phase and an effective reduction, along at least one transverse section of the multichannel capillary column, in the average distance traveled by sample molecules during diffusion to reach a proximate portion of the stationary phase.

In another aspect of the present invention, the interior wall of the multichannel capillary column is constructed to provide the capacity of a large bore capillary column and the speed and resolution of a small bore capillary column. The interior wall of the multichannel capillary column, however, includes a single internal bore having a plurality of channels, wherein adjacent channels are partially separated by a respectively interposed ridge, and the surfaces of the channels and ridges include a stationary phase coating.

In another aspect of the present invention, n channels are evenly distributed about the central longitudinal axis of the column. When n refers to an even number, first and second imaginary axes of symmetry may be understood to distinguish the internal geometry of the n channels and n ridges, such that each of then channels exhibit identical, or nearly identical, cross-sectional dimensions. When n refers to an odd number, there are corresponding first, second, . . . n imaginary axes of symmetry that may be seen to distinguish the internal geometry of the n channels and n ridges.

In another aspect of the present invention, the internal geometry of the interior wall is accordingly symmetrical about such axes of symmetry such that each of the n internal channels preferably exhibit identical or nearly identical, and at least functionally equivalent, cross-sectional dimensions so as to achieve uniform separation characteristics among the channels of the multichannel capillary column.

In another aspect of the present invention, most, if not all, of the non-uniformity of the separation characteristics of the channels, due to, e.g., slight dimensional differences, irregularities in the stationary phase thickness, aging, etc., will be minimized because of the capability for cross-channel diffusion of the sample.

As a result, the multichannel capillary column generally lacks the disadvantages described hereinabove with respect to a conventional single capillary column, or a multicapillary column.

DETAILED DESCRIPTION OF THE PREFERRED EMBODIMENT

The present invention will find useful application in a variety of analytical systems that benefit from analysis of one or more fluid streams.

The multichannel capillary column of the present invention may be employed in particular to provide separation with respect to one or more of such fluid streams. Gases are the preferred fluids according to the practice of the present invention, and therefore the following description of the invention will include a description of the arrangement, construction, and operation of a multichannel capillary column suitable for use in an analysis of a gaseous stream in a gas chromatographic analytical system (hereinafter, a chromatography. However, for the purposes of the following description, the term "fluid" will also be considered to refer to all types of fluids.

It should be understood that the teachings herein are applicable to other analytical instruments, including liquid chromatographs, high-pressure gas chromatographs (HPGC), high pressure liquid chromatographs (HPLC), supercritical fluid chromatographs (SFC), and supercritical fluid extraction (SFE) instruments.

In the Figures and in the description to follow, like nomenclature and numeric identifiers will refer to like components; and virtual or imaginary components such as imaginary lines or axes are schematically drawn in dashed lines.

Figure 1:
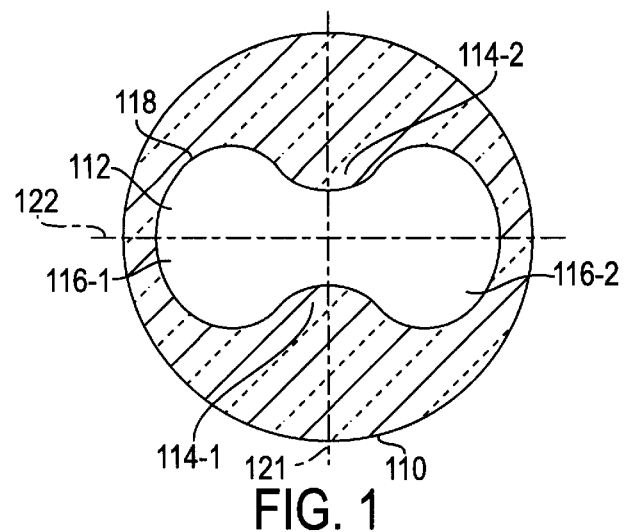
FIG. 1 is a simplified cross-sectional view of a novel multichannel capillary column constructed in accordance with the present invention.

A new and novel multichannel capillary column is shown in FIG. 1 and is generally designated as capillary column 120. The capillary column 120 is provided with an interior wall 118 having therein a plurality of internal, small diameter channels such that, in comparison to a conventional column, the capillary column 120 offers substantial improvements in sample capacity without sacrificing analytical speed and resolution. For the purposes of this description, the multichannel capillary column 120 incorporates a single interior bore 112 defined by the interior wall 118. The interior wall 118 includesn opposing ridges 114-1, 114-2, . . . 114-n that partially separate adjacent pairs of channels 116-1,116-2, . . . 116-n. In the illustrated embodiment, n is equal, but need not be limited, to two. The opposing ones of ridges 114-1, 114-2, . . . 114-n are radially distributed, with their innermost portions being separated by a gap. Accordingly, a central, coaxial portion of the bore 112 allows cross-channel fluid communication between all of the n internal channels 116-1,116-2, . . . 116-n.

In the embodiment illustrated in FIG. 1, whereinn refers to two, which is an even number, there are first and second axes of symmetry 121,122, that may be drawn to illustrate the internal geometry of the interior bore 112. (With reference also to FIG. 3, first and second axes of symmetry 321, 322, also may be understood to illustrate the interior wall of the interior bore 312.) Those skilled in the art will appreciate that the internal geometry of the interior wall 118 is accordingly symmetrical about such axes 121,122 such that each of the n internal channels 116-1,116-2, . . . 116-n preferably exhibit identical or nearly identical, and at least functionally equivalent, cross-sectional dimensions so as to achieve uniform separation characteristics among substantially all channels of the multichannel capillary column. Accordingly, it is also preferred that each of the n internal channels 116-1,116-2, . . . 116-n define identical or nearly identical, and at least functionally similar, cross-sectional areas when viewed along a transverse section of the column 110. Also, each of then internal channels 116-1,116-2, . . . 116-n preferably exhibit identical or nearly identical, and at least functionally equivalent, stationary phase coating compositions and thicknesses.

Figure 2:
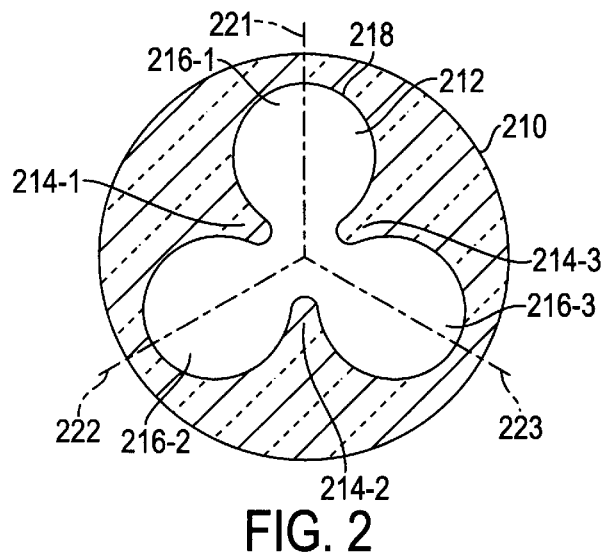
FIGS. 2–3 are simplified cross-sectional views of respective second and third preferred embodiments of a multichannel capillary column constructed in accordance with the present invention.
Figure 3:
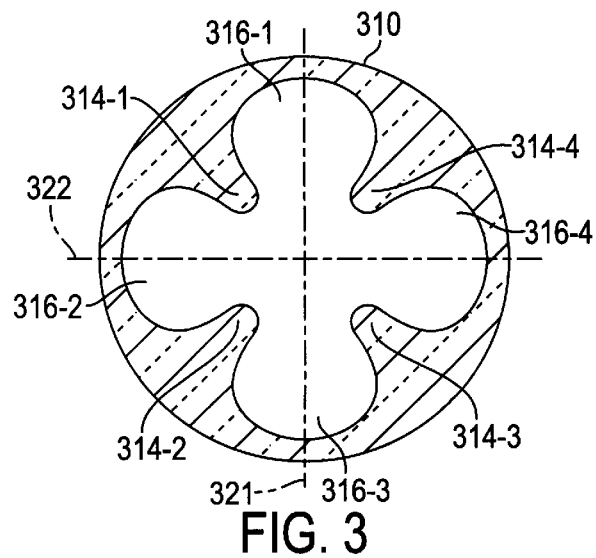

With reference to FIGS. 2 and 3, additional second and third preferred embodiments of capillary columns 210, 310 will be understood. In FIG. 2, a second embodiment of a multichannel capillary column 210 may be constructed to include an interior wall 218 defining an interior bore 212 having three evenly distributed ridges 214-1, 214-2, 214-3 so as to distinguish three internal channels 216-1, 216-2, 216-3. Cross-channel fluid communication is maintained between all of the internal channels 216-1, 216-2, 216-3. The interior wall 218 of the interior bore 212 is preferably coated with a stationary phase as known in the art. In the illustrated embodiment, whereinn refers to an odd number, first, second, and third imaginary axes of symmetry 221, 222,223 may be drawn to illustrate the geometry of the interior bore 212.

As illustrated in FIG. 3, a third embodiment of a multichannel capillary column 310 includes an interior bore 312 and an interior wall 318 having four opposing ridges 314-1, 314-2, 314-3, 314-4 so as to distinguish four internal channels 316-1, 316-2, 316-3, 316-4. Cross-channel fluid communication is maintained between all of the internal channels 316-1, 316-2, 316-3, 316-4. The interior wall 318 is preferably coated with a stationary phase as known in the art. In the illustrated embodiment, whereinn refers to four (an even number), first and second imaginary axes of symmetry 321,322, may be drawn to illustrate the geometry of the interior bore 312.

Those skilled in the art will now appreciate that, according to the teachings of the present invention, a multichannel capillary column may be constructed to integrate a plurality of evenly-distributed, partially-separated, parallel channels, all of which have continuous cross-channel fluid communication therebetween. This capability for cross-channel diffusion in the multichannel capillary column construction described herein greatly reduces the effects of channel-to-channel disparities due to any dimensional asymmetries in the multichannel capillary column. The capability for cross-channel diffusion in the multichannel capillary column construction described herein also minimizes the effects of channel-to-channel disparities in the respective portions of the stationary phase coating in each channel. This capability for cross-channel diffusion also minimizes, by equilibration of fluid pressure, any inconsistency or difference in the flow rates of the fluid flows in each of the channels. Furthermore, this provision of a plurality of symmetrically-disposed, partially separated, parallel channels, wherein each pair of adjacent channels is separated by a respective ridge, greatly increases the total surface area of the stationary phase coating. The foregoing advantages are realizable in comparison to a conventional capillary column of similar exterior dimensions and constructed according to the prior art.

Preferred embodiments of a multichannel capillary column may be constructed by drawing a hollow tube of fused silica using a shaped mandrel to produce the desired number, configuration, and size of ridges and channels within a column bore of an appropriate dimension. The newly drawn silica column is of course preferably provided with a protective coating or coatings on its exterior surface so as to protect the column from abrasion and moisture, as known in the art. The internal surface of the column may be deactivated and optionally provided with a stationary phase coating according to techniques known in the art.

Those skilled in the art will appreciate that a multichannel capillary column may be constructed to include more than the four channels 316-1, 316-2, 316-3, 316-4 shown in FIG. 3. A greater number of ridges and channels are contemplated as being within the scope of this invention. A potential limitation on the number of channels is expected to be determined by such factors as the manufacturability of the tools needed for drawing the fused silica, the number and mechanical strength of the ridges, and so on.

In sharp contrast to the multi-capillary column designs in the prior art which, for example, employ a bundle of discrete columns, a multichannel capillary column constructed according to the teachings herein will exhibit a smooth cylindrical exterior that is indistinguishable from the exterior of a conventional capillary column of comparable exterior dimensions. Preferred embodiments of the multichannel capillary column may accordingly be easily terminated or connected to ancillary equipment by use of known fittings, connectors, and the like in the conventional manner.

While the invention has been described and illustrated with reference to specific embodiments, those skilled in the art will recognize that modification and variations may be made without departing from the principles of the invention as described herein above and set forth in the following claims.

What is claimed is:

1. A multichannel capillary column having an interior wall defining a single internal bore, wherein the interior wall forms a plurality of n channels and n ridges wherein adjacent channels are partially separated by a respectively interposed ridge and wherein a central, coaxial portion of the internal bore communicates with each of channels to allow cross-channel fluid communication between all of the n channels.

2. The multichannel capillary column of claim 1, wherein the interior wall further includes an internal coating of stationary phase on the surfaces of the channels and ridges.

3. The multichannel capillary column of claim 1, wherein each of then internal channels exhibit functionally equivalent cross-sectional dimensions so as to achieve uniform separation characteristics among the channels of the multichannel capillary column.

4. The multichannel capillary column of claim 1, wherein the n channels are evenly distributed about a central longitudinal axis of the column and, in an instance wherein n refers to an even number, first and second imaginary axes of symmetry may be drawn to distinguish the internal geometry of the n channels and n ridges, and in an instance wherein n refers to an odd number, corresponding first, second, . . . n imaginary axes of symmetry may be drawn to distinguish the internal geometry of then channels and n ridges, and wherein each of the n channels exhibit substantially identical cross-sectional dimensions and are symmetrical about their respective axes of symmetry.

5. The multichannel capillary column of claim 1, wherein a transverse section of the column may be obtained to determine the cross-sectional area defined by each of the channels, and wherein the resulting cross-sectional areas of the channels are substantially equal.

6. The multichannel capillary column of claim 1, wherein n equals a number in the range of 2 to 4.

7. The multichannel capillary column of claim 1, wherein the interior wall further comprises a fused silica composition.

8. A method of making a multichannel capillary column, comprising the steps of:

forming an interior wall with a plurality of n channels and n ridges, wherein the adjacent channels are partially separated by a respectively interposed ridge such that an internal bore is formed having a central, coaxial portion that communicates with each of the channels, whereby cross-channel fluid communication is established between all of the n channels.

9. A multichannel capillary column having an interior wall defining a single internal bore that can be encompassed by a circle having a diameter 1mm, wherein the interior wall forms a plurality of n channels and n ridges wherein adjacent channels are partially separated by a respectively interposed ridge and wherein a central, coaxial portion of the internal bore communicates with each of the channels to allow cross-channel fluid communication between all of the n channels.

* * * * *